United States Patent [19]

Riley et al.

[11] Patent Number: 4,692,875

[45] Date of Patent: Sep. 8, 1987

[54] METAL ALLOY IDENTIFIER

[75] Inventors: William D. Riley; Robert D. Brown, Jr., both of Avondale, Md.

[73] Assignee: The United States of America as represented by the Secretary of the Interior, Washington, D.C.

[21] Appl. No.: 623,753

[22] Filed: Jun. 22, 1984

[51] Int. Cl.$^4$ .......................... G01J 3/06; G01J 3/30; G06F 15/46

[52] U.S. Cl. .................................. 364/497; 356/308; 356/313

[58] Field of Search ...................... 364/497, 550, 560; 356/313, 328, 308, 326, 417, 407

[56] References Cited

U.S. PATENT DOCUMENTS

| | | | |
|---|---|---|---|
| 3,547,542 | 12/1970 | Bulpitt et al. | 356/308 |
| 3,588,257 | 6/1971 | Folsom et al. | 356/417 |
| 3,791,743 | 2/1974 | Cody et al. | 356/36 |
| 3,909,133 | 9/1975 | Hobson et al. | 356/313 |

Primary Examiner—Errol A. Krass
Assistant Examiner—Danielle Laibowitz
Attorney, Agent, or Firm—Thomas Zack; E. Philip Koltos

[57] ABSTRACT

To identify the composition of a metal alloy, sparks generated from the alloy are optically observed and spectrographically analyzed. The spectrographic data, in the form of a full-spectrum plot of intensity versus wavelength, provide the "signature" of the metal alloy. This signature can be compared with similar plots for alloys of known composition to establish the unknown composition by a positive match with a known alloy. An alternative method is to form intensity ratios for pairs of predetermined wavelengths within the observed spectrum and to then compare the values of such ratios with similar values for known alloy compositions, thereby to positively identify the unknown alloy composition.

18 Claims, 4 Drawing Figures

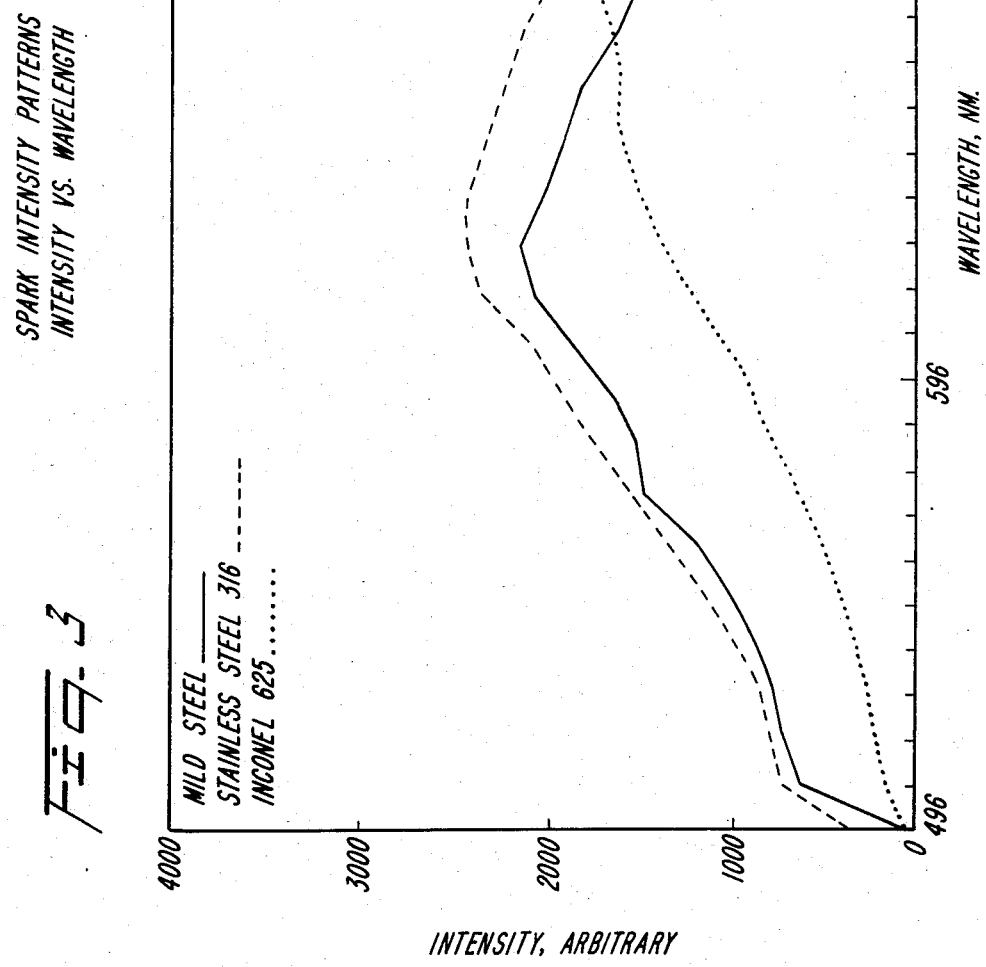

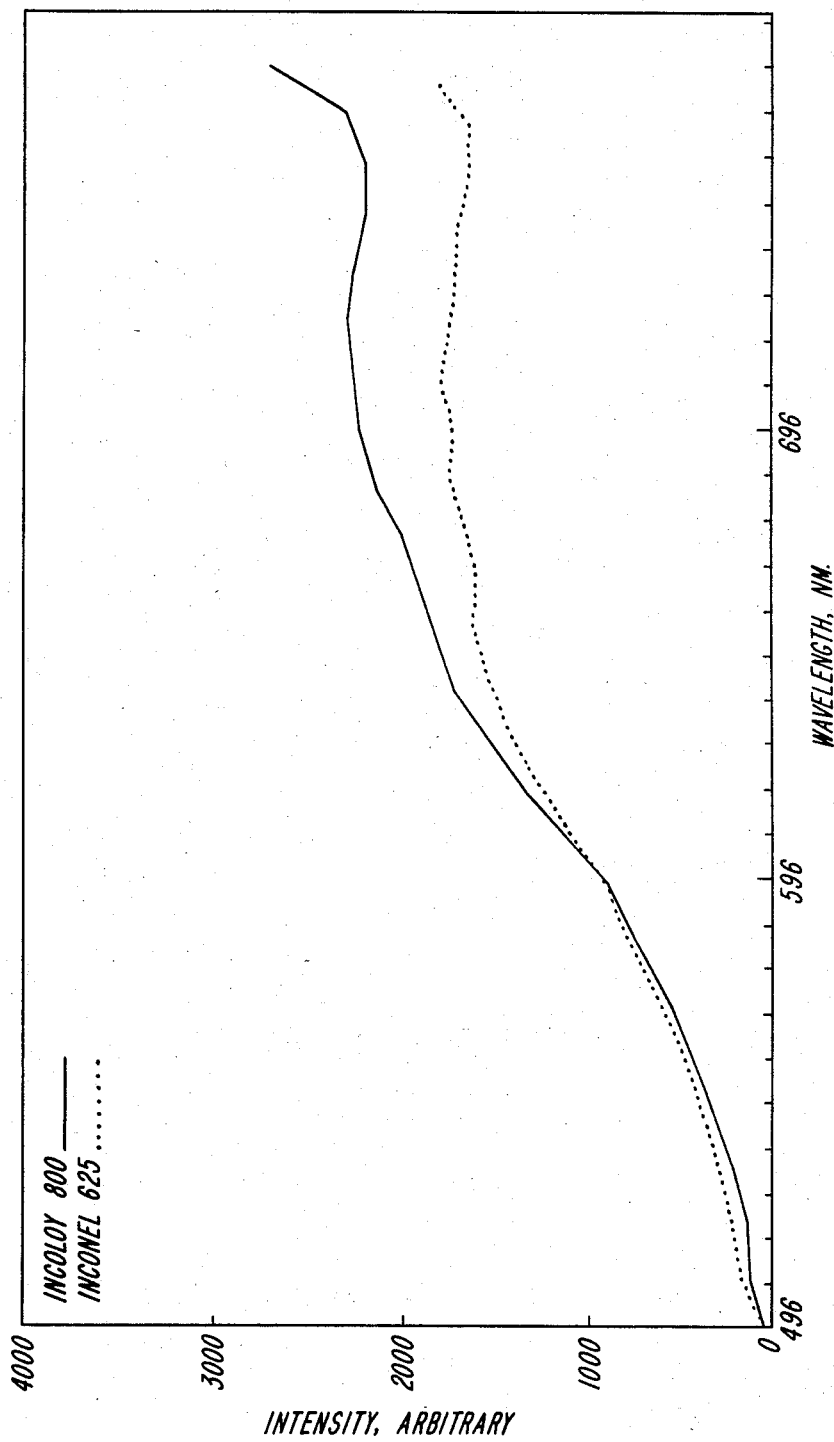

METAL ALLOY IDENTIFIER

BACKGROUND OF THE INVENTION

1. Field of the Invention

This invention relates generally to apparatus and methods for segregation of scrap metal pieces by identification of their individual alloy compositions, and more particularly, to identification of alloy compositions by optical analyses of sparks generated therefrom.

2. Background of the Invention

The science of spectroscopy involves detailed analyses of wavelength spectra characterizing the electromagnetic radiation given off by heated bodies, and it has long been known that heated metal alloys emit such electromagnetic radiation in colors related to the constituent elements in their alloy compositions. When an alloy is sufficiently heated, each constituent element emits visible light primarily at a characteristic wavelength, i.e., has its own visually observable signature. The intensity of the emission from each element, at its characteristic wavelength, is relatable to the proportion in which that element is present in the alloy being examined.

It has also been known for a long time, as indicated by the literature cited below, that the color and shape of the spark pattern given off when a grinding wheel is applied to a metal piece can be related to the metal composition. This is simply because the sparks are really only very small glowing pieces of the metal heated to very high temperatures by the rapid input of mechanical energy from the grinding wheel which tears them off the parent metal piece. The use of this technique has been limited by the availability of skilled individuals, who must rely solely on personal experience and judgment to identify metal alloys by the color and shape of the spark pattern. In the prior art, to date, the utilization of spectral information in metal-grinding sparks has been based on and limited to subjective sensory impressions, which precludes distinguishing among alloys with minor compositional differences.

All of the high-nickel superalloys, for example, are characterized by a short, red spark and cannot be separated using the conventional subjective technique. Such alloys generally are identified by sophisticated laboratory techniques requiring skilled personnel qualified in emission spectroscopy, fluorescent x-ray spectroscopy, or atomic absorption spectroscopy and the like. The apparatus and methods taught in this invention, however, can precisely and easily separate such superalloys into individual alloys, on the basis of relatively subtle spectral differences in the sparks ground off from them.

This invention, therefore, is intended to enable even unskilled persons to easily, rapidly and accurately identify scrap metal pieces by their different alloy compositions, thereby to correctly segregate them for subsequent reprocessing.

Allen et al U.S. Pat. No. 4,269,507 pulverizes solids with a grindstone and injects propelled particles into a flame for analysis by a mass spectrometer. The cone of the mass spectrometer must be placed into the flame to analyze the content of the propelled particles.

In Vreeland U.S. Pat. No. 2,751,811 the spectrum of a sample is compared with a standard spectrogram by heating the sample to incandescence in an electric arc, and exposing the glowing pieces to a spectrograph. Neither approach is suitable for unskilled personnel outside a laboratory or other controlled environment.

SUMMARY OF THE INVENTION

Accordingly, one subject of this invention is the provision of novel apparatus for identifying metal pieces by their different alloy compositions.

A more specific object of this invention is the provision of rugged apparatus, suitable for use by relatively unskilled persons working in scrapyards or at demolition sites, to easily, rapidly and accurately segregate metal scrap pieces by their different alloy compositions.

Another object of this invention is the provision of a novel method for distinguishing among standard metal alloys on the basis of their constituents.

A related object of this invention is the provision of a method for distinguishing among metal alloys which contain the same constituents but in different proportions.

These and other objects are provided in accordance with the invention by generating sparks from a sample of the metal alloy, viewing the sparks with an optical probe to generate a multi-wavelength visual signal and dividing the signal into separate parts. The separate parts of the multi-wavelength visual signal are filtered by single wavelength optical filters, and the intensities of the filtered signals are detected. Ratios of the measured intensities are compared in a data processing means with other measured intensities.

In accordance with more specific aspects of the hot glowing invention, the sparks are generated from the surface of the alloy solely by impinging against the surface a rotating grinding wheel. This is in contrast with prior art techniques involving application of an external source of energy, such as a flame or arc, to heat the metal particles to incandescence.

In accordance with other aspects of the invention, the incandescent sparks are exposed to a rapid scanning spectrometer and a photomultiplier tube or self-scanning diode array, to determine the intensity distribution of a function of wavelength of the signal analyzed by the spectrometer.

Still other objects and advantages of the present invention will become readily apparent to those skilled in this art from the following detailed description, wherein we have shown and described only the preferred embodiments of the invention, simply by way of illustration of the best modes contemplated by us of carrying out our invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

A more complete appreciation of the invention and many of its attendant advantages will be readily obtained as the same become better understood by reference to the following detailed description when considered in connection with the accompanying drawings, wherein:

FIG. 3 is a graphical depiction of spark intensity patterns, shown as plots of intensity versus wavelength, for Mild Steel, Stainless Steel 316 and Inconel 625.

FIG. 4 is a graphical depiction of spark intensity patterns, shown as plots of intensity versus wavelength, for nickel alloys Incoloy 800 and Inconel 625.

DESCRIPTION OF THE PREFERRED EMBODIMENTS

Figure 1:
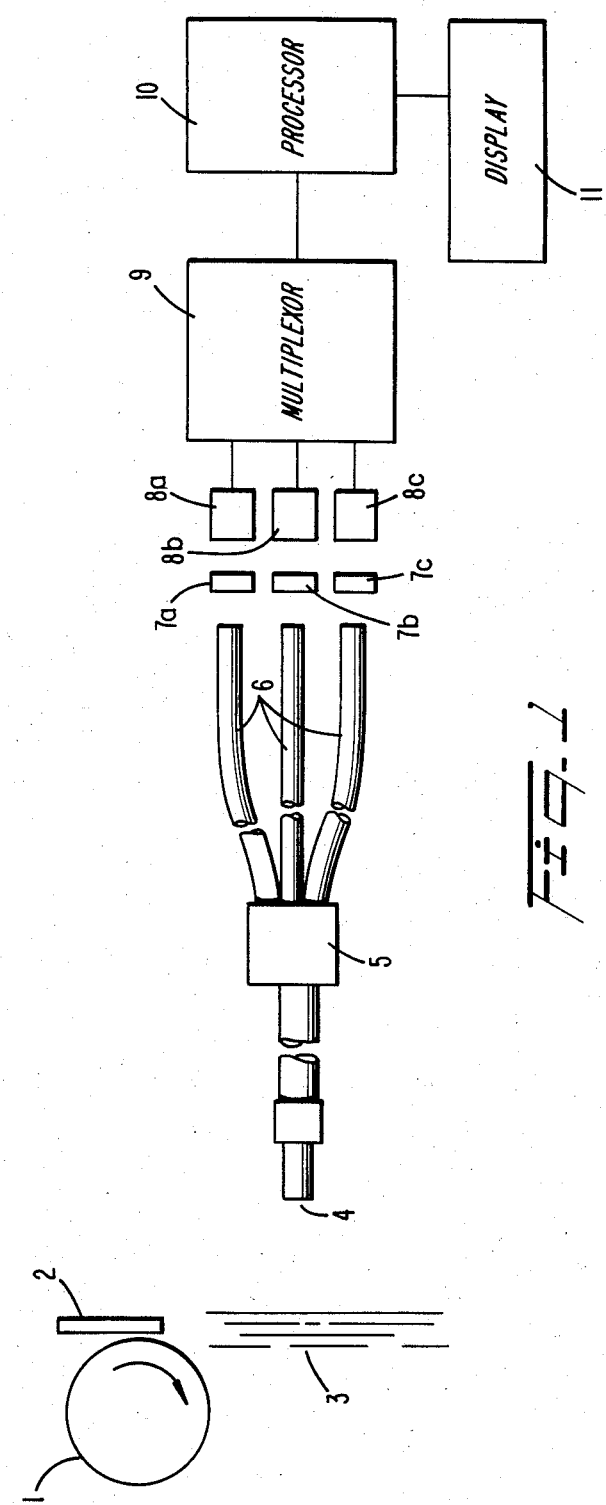
FIG. 1 is a block diagram showing the principal elements of the apparatus of the invention in one of its embodiments.

The embodiment shown in FIG. 1 (Embodiment A, hereafter) includes a spark generating means 1, e.g., a conventional grinding wheel, to generate from a metal piece 2 a pattern of sparks 3 for viewing by an adjacently positioned fiber-optic collimating probe 4, such as the Oriel 77644. The light received from sparks 3 by probe 4 is conveyed to an attached trifurcated fiber optic probe 5, such as the Oriel 77536 which has a three-way splitter whose three branches 6 transmit equal amounts of light to three transmission filters 7a, 7b, and 7c. The light received by these three filters is composed of light of many wavelengths, but each individual filter passes on a transmission of only one wavelength.

The three transmission filters 7a, 7b, and 7c preferably are of wavelengths 450, 550, and 650 nanometers (nm hereinafter), such as the Oriel 5383, 5389, and 5395 respectively, each within a tolerance of ±5 (nm). Note that the three selected wavelengths are all in the visible light spectrum. These single wavelength transmissions are then conveyed to three cooperating high-speed silicon detectors 8a, 8b, and 8c, such as the Oriel 7180-1, each of which measures the intensity of the light it receives at one of the three preferred wavelengths. The intensities of light the selected at different wavelengths constitute the raw data, which corresponds to the constituents of the alloy from which the observed sparks originated. These data are then conveyed from detectors 8a, 8b, and 8c to a cooperating multiplex unit 9, such as the Dataplex 10 manufactured by Omega Engineering, which with associated electronic data processor 10 of conventional type generates ratios of the light the selected intensities for different pairs of the three preferred wavelengths. Comparisons based on ratios of intensities at specific wavelengths are free of biases caused by differences in probe orientation and spark brightness in the course of physically obtaining the data. These ratios may be displayed on a conventional CRT display unit 11, such as a Keithly 177 DVM or the Hewlett-Packard 3437A DVM, and may be used, as more fully explained below, to identify the alloy of which metal piece 2 is composed.

Figure 2:
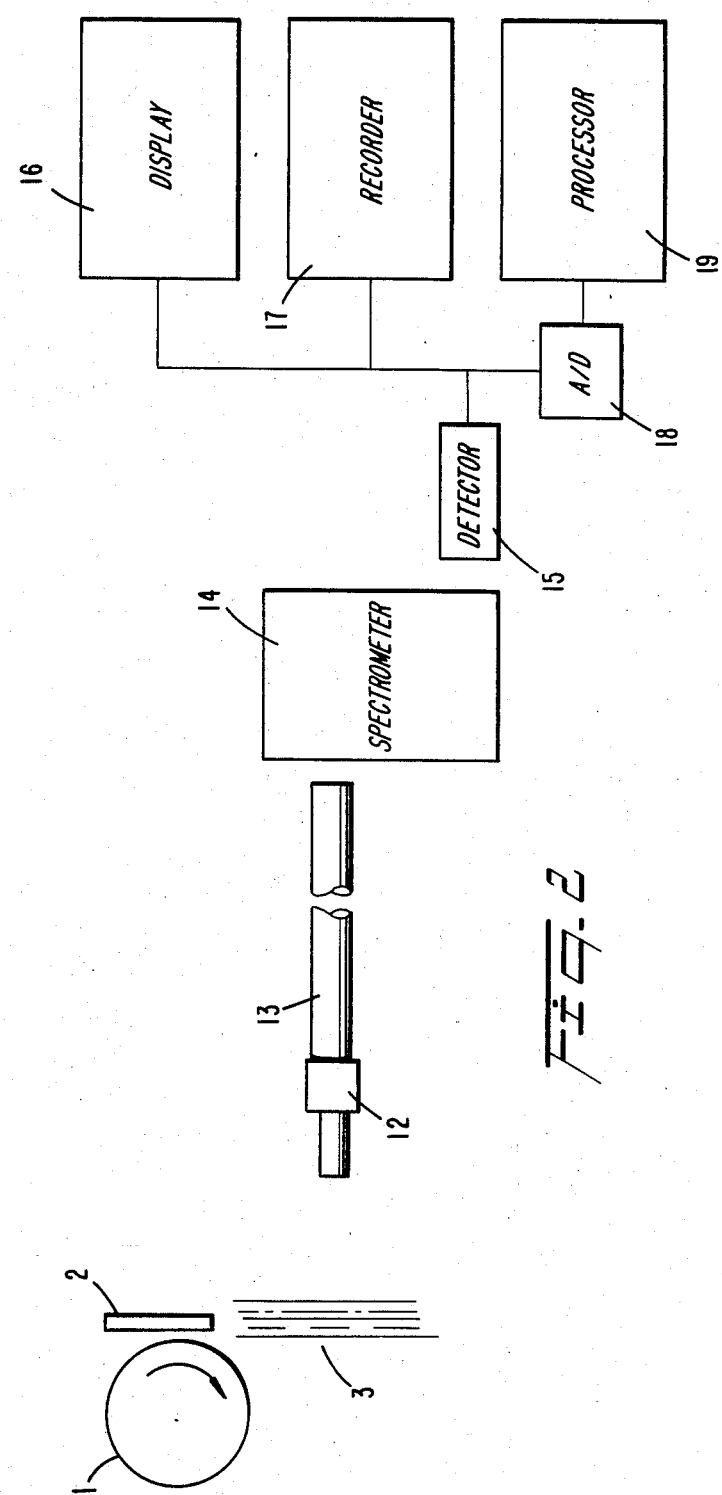
FIG. 2 is a block diagram showing the principal elements of the apparatus in an alternative embodiment of the invention.

An alternative embodiment (Embodiment B, hereinafter), as shown in FIG. 2, includes, as before, a spark generating means 1 to generate from a metal piece 2 a pattern of sparks 3, observed by a collimating probe 12, such as the Oriel 77644, which transmits the observed visual signal to attached fiber optic probe 13 such as the Oriel Optic Cable 77547, which conveys the signal to a cooperating rapid scanning spectrometer 14, such as the Model 6000 Spectrolizer manufactured by Rolfin. The wavelength spectrum of the light from the observed sparks, i.e., the observed visual signal, is determined in the spectrometer 14. The light is then transmitted directly to a high speed silicon detector 15, such as the Model R928 manufactured by Rolfin, and from it to a conventional CRT display unit 16, and, optionally, to a conventional strip-chart recorder 17, such as the Hewlett-Packard 7470AXY plotter, to record the data in analog form.

Other embodiments utilizing functional equivalents of assorted elements of the apparatus will no doubt occur to persons skilled in the art who are interested in practicing this invention. Thus, for example, in FIG. 2 a photo-multiplier tube may be used in place of silicon detector (Embodiment C, hereinafter). Furthermore, the data being recorded by recorder 17 may be digitized for subsequent analysis or, for more immediate use, may be converted in an optical analog-to-digital converter 18, such as the Hewlett-Packard 3745A digital voltmeter or the Tracor Northern TN 1710 signal analyzer, for real time analysis and prompt alloy identification by a conventional computer 19, such as a Hewlett-Packard 9816 microcomputer or the LSI 11 microcomputer.

In yet another embodiment of the apparatus, the rapid-scanning spectrometer 14 and high-speed silicon detector of Embodiment B above are replaced by a spectrometer and a self-scanning diode array, acting in combination with the spark observing and light transmitting elements, to examine the entire wavelength spectrum of the light given off by sparks 3 (Embodiment D hereinafter).

Apparatus as described for Embodiment D was used in actually reducing the invention to practice, and full-spectrum data were obtained on four metallic compositions of interest: Mild Steel, Stainless Steel 316, Inconel 625 and Incoloy 800. Plots of intensity (to an arbitrary scale) versus wavelength (nm) are shown for these materials in FIGS. 3 and 4. It is clear from these that each alloy has its own distinctive "signature" on such a plot. Such information on a large number of alloys may be stored as a library, in the memory of computer 19 for example, to provide references with which the spark analysis signature of an observed metal alloy may be compared for easy, rapid and accurate identification of its composition.

Data from apparatus described in Embodiment A above (as shown in FIG. 1), constituting intensity values measured on a common scale at the three preferred wavelengths of 450, 550, and 650 (nm) were obtained experimentally for four materials of interest. The results are tabulated below in Table 1. Ratios of the intensities for two pairs of wavelengths also were computed for these materials and are tabulated below in Table 2.

TABLE 1

| | Intensities at Indicated Wavelengths | | |
|---|---|---|---|
| | Wavelengths | | |
| Alloys | 450 (nm) | 550 (nm) | 650 (nm) |
| Armco DQ Mild Steel | 0.30 | 1.4 | 1.1 |
| Armco Formable HSLA Steel | 0.33 | 1.4 | 1.1 |
| 316 Stainless Steel | 0.18 | 0.37 | 0.52 |
| Inconel 625 | 0.04 | 0.15 | 0.40 |

TABLE 2

| | Ratios of Intensities at Indicated Wavelengths | |
|---|---|---|
| | Intensity ratios | |
| Alloys | at 450 (nm)/ at 650 (nm) | at 550 (nm)/ at 650 (nm) |
| Armco DQ Mild Steel | 0.25 | 1.3 |
| Armco Formable HSLA Steel | 0.30 | 1.5 |
| 316 Stainless Steel | 0.35 | 0.71 |
| Inconel 625 | 0.10 | 0.38 |

In practice, small samples of large and unwieldy pieces of scrap metal may be brought to a bench grinder and the spark intensity values and their ratios can be compared to tabulated values of like alloys to identify the composition of the metal in question. Alternatively, the data as full-spectrum plots of intensity versus wavelength, to some standardized scale, may be compared by means of a computer, in real time, with a library of such plots for likely alloys. Where the convenience of indoor generation and analysis of data is not feasible, the apparatus as a unit may be carried to the scrap metal site and the data recorded for later study or analyzed on the spot by means of a conventional programmable portable microprocessor.

Persons skilled in the art will recognize the utility of these and other variations that are possible in both the apparatus and methods of use disclosed herein without departing from the scope of this invention. It is, therefore, to be understood that numerous additional modifications and variations of the present invention are possible in light of the above teachings, and that within the scope of the appended claims the invention may be practiced otherwise than as described herein.

What we claim is:

1. An apparatus for identifying a metal alloy comprising:
   a grinding wheel adapted to be applied against a surface of a sample of the metal alloy and rotated to generate solely by said application glowing hot sparks from the surface;
   an optical probe exposed to said glowing hot sparks and adapted to generate a multiwavelength visual signal therefrom;
   signal dividing means for dividing the multiwavelength visual signal into separate parts;
   filter means for filtering the separate parts of said divided multiwavelength visual signal;
   detector means for measuring respective intensities of the single wavelength filtered signals; and
   data processing means coupled to the detector means for generating ratios of the measured intensities with respect to at least one other of the measured intensities.

2. An apparatus for identifying a metal alloy as specified in claim 1, further comprising:
   a display means coupled to said data processing means for displaying said ratios for convenient comparison with similar ratios for alloys of known composition.

3. An apparatus for identifying a metal alloy as specified in claim 1, further comprising:
   recording means cooperating with said data processing means to permanently record said ratios.

4. An apparatus for identifying a metal alloy as specified in claim 1, wherein:
   said single-wavelength filters pass visual signals at 450 (nm), 550 (nm) and 650 (nm) wavelengths, respectively, within a tolerance of ±5 (nm) on each.

5. An apparatus for identifying a metal alloy, comprising:
   a grinding wheel adapted to be applied against a surface of a sample of the metal alloy and rotated to generate solely by said application glowing hot sparks from a sample of said metal alloy;
   a cooperating optical probe to generate a multiwavelength visual signal by viewing said glowing hot sparks;
   a rapid-scanning spectrometer coupled to said optical probe to analyze said multiwavelength visual signal therefrom;
   a high-speed silicon detector cooperating with said rapid-scanning spectrometer to determine an intensity distribution as a function of wavelength in said analyzed visual signal; and
   a display means coupled to said silicon detector for conveniently displaying said intensity distribution as a function of wavelength for convenient comparison with standardized data for known alloys.

6. An apparatus for identifying a metal alloy as specified in claim 5, further comprising:
   a strip chart recorder cooperating with said silicon detector to permanently record said intensity distribution as a function of wavelength.

7. An apparatus for identifying a metal alloy, comprising:
   a grinding wheel adapted to be applied against a surface of a sample of the metal alloy and rotated to generate solely by said application glowing hot sparks from a sample of said metal alloy;
   a cooperating optical probe to generate a multiwavelength signal by viewing said glowing hot sparks;
   a rapid-scanning spectrometer coupled to said optical probe to analyze said multiwavelength visual signal therefrom;
   a photomultiplier tube cooperating with said rapid-scanning spectrometer to determine an intensity distribution as a function of wavelength in said analyzed signal; and
   a display means coupled to said photomultiplier tube for conveniently displaying said intensity distribution as a function of wavelength for convenient comparison with standardized data for known alloys.

8. An apparatus for identifying a metal alloy as specified in claim 7, further comprising:
   a strip chart recorder cooperating with said photomultiplier tube to permanently record said intensity distribution as a function of wavelength.

9. An apparatus for identifying a metal alloy, comprising:
   a grinding wheel adapted to be applied against a surface of a sample of the metal alloy and rotated to generate solely by said application glowing hot sparks from a sample of said metal alloy;
   a cooperating optical probe to generate a multiwavelength visual signal by viewing said glowing hot sparks;
   a spectrometer coupled to said optical probe to analyze said multiwavelength visual signal therefrom;
   a self-scanning diode array cooperating with said spectrometer to determine an intensity distribution as a function of wavelength in said analyzed signal;
   an analog-to-digital converter cooperating with said diode array to digitize the data output therefrom; and
   data processing means coupled to said analog-to-digital converter for real-time processing of said digitized data for convenient comparison with standardized data for known alloys.

10. An apparatus for identifying a metal alloy as specified in claim 9, further comprising:
    recording means cooperating with said data processing means to permanently record said processed digitized data.

11. A method for identifying a metal alloy, comprising the steps of:
- applying a rotating grinding wheel to a sample of said metal alloy to generate solely by said application glowing hot sparks from said metal alloy;
- generating a multiwavelength visual signal by viewing said glowing hot sparks;
- dividing said multiwavelength visual signal into separate parts;
- filtering said separate parts of said multiwavelength visual signal for predetermined single wavelengths;
- measuring respective intensities of said single wavelength filtered signals;
- forming ratios of said respective intensities for predetermined pairs of single wavelengths; and
- comparing said ratios for said alloy with similar ratios for alloys of known compositions to establish a match for said metal alloy.

12. A method for identifying a metal alloy as specified in claim 11, further comprising the step of:
- permanently recording said ratios for said metal alloy.

13. A method for identifying a metal alloy as specified in claim 11, wherein:
- said filtering of said equal parts of said multiwavelength visual signal is performed at wavelengths of 450 (nm), 550 (nm) and 650 (nm) within a tolerance of ±5 (nm) on each.

14. A method for identifying a metal alloy, comprising the steps of:
- applying a rotating grinding wheel to a sample of said metal alloy to generate solely by said application glowing hot sparks from said metal alloy;
- generating a multiwavelength visual signal by viewing said glowing hot sparks;
- spectrographically determining an intensity distribution as a function of wavelength in said multiwavelength visual signal; and
- comparing said intensity distribution as a function of wavelength for said alloy with similar intensity distributions for alloys of known compositions to establish a match for said metal alloy.

15. A method for identifying a metal alloy as specified in claim 14, including:
- transforming said intensity distribution as a function of a wavelength for said metal alloy from analog to digital data form for comparison with said similar intensity distributions also in digital data form for alloys of known compositions to establish a match for said metal alloy.

16. A method for identifying a metal alloy as specified in claim 15, further comprising the step of:
- permanently recording said intensity distribution as a function of wavelength for said metal alloy in digital data form.

17. A method for identifying a metal alloy as specified in claim 14, further comprising the step of:
- permanently recording said intensity distribution as a function of wavelength for said metal alloy.

18. A method for identifying a metal alloy, comprising:
- impinging a rotating grinding wheel against a surface of the solely by said impingement metal alloy to cause glowing hot sparks to be generated from said surface;
- generating a multi-wavelength visual signal from said glowing hot sparks;
- dividing the multi-wavelength visual signal into separate parts;
- filtering the separate parts of the multi-wavelength visual signal for predetermined signal wavelengths;
- measuring respective intensities of said single wavelength filter signals;
- forming ratios of the respective intensities for predetermined pairs of single wavelengths; and
- comparing the ratios for said alloy with similar ratios for alloys of known compositions to establish a match for said metal alloy.

* * * * *